(12) United States Patent
Petrov et al.

(10) Patent No.: US 9,389,193 B1
(45) Date of Patent: Jul. 12, 2016

(54) SPATIALLY RESOLVED MAGNETIC RESONANCE SPIN-SPIN RELAXATION DISTRIBUTION MEASUREMENT METHODS

(75) Inventors: Oleg Petrov, Fredericton (CA); Bruce Balcom, Fredericton (CA)

(73) Assignee: University of New Brunswick, Fredericton, New Brunswick (CA)

( * ) Notice: Subject to any disclaimer, the term of this patent is extended or adjusted under 35 U.S.C. 154(b) by 784 days.

(21) Appl. No.: 13/571,954

(22) Filed: Aug. 10, 2012

Related U.S. Application Data

(60) Provisional application No. 61/522,978, filed on Aug. 12, 2011.

(51) Int. Cl.
*G01N 24/08* (2006.01)
*G01R 33/44* (2006.01)

(52) U.S. Cl.
CPC .............. *G01N 24/08* (2013.01); *G01R 33/446* (2013.01); *G01R 33/448* (2013.01)

(58) Field of Classification Search
CPC .. G01R 33/54; G01R 33/307; G01R 33/5602; G01R 33/46; G01R 33/4828; G01R 33/5607; G01R 33/50; G01R 33/5617; G01R 33/448; G01N 24/081; G01N 24/085; G01N 24/08
USPC ........... 324/303, 307–309; 600/410, 413, 419
See application file for complete search history.

(56) References Cited

U.S. PATENT DOCUMENTS

| | | | |
|---|---|---|---|
| 5,099,207 A * | 3/1992 | Luyten | G01R 33/4833 324/309 |
| 5,412,320 A | 5/1995 | Coates | |
| 6,242,912 B1 | 6/2001 | Prammer et al. | |
| 6,512,371 B2 | 1/2003 | Prammer | |
| 6,833,699 B2 | 12/2004 | Galford et al. | |
| 7,869,565 B2 | 1/2011 | Wood et al. | |
| 2008/0024128 A1 * | 1/2008 | Song | G01N 24/081 324/307 |
| 2011/0181283 A1 * | 7/2011 | Grinstead | G01R 33/5635 324/309 |

FOREIGN PATENT DOCUMENTS

CA 2646456 A1 4/2008

OTHER PUBLICATIONS

Oleg V. Petrov, et al., T2 Distribution Mapping Profiles with Phase-Encode MRI, J. Magn. Reson. 209(1): 39-46, Mar. 2011.
Aura Tintaru, et al., E-BURP-2 Excitation in the CPMG Sequence for Improving Reliability of Relaxation Data in the Study of Guest/Host Interactions in Inclusion Complexes in Water, Chem. Phys. Letters 381(3-4), 458-463, Nov. 2003.
Rieko Ishima, et al., Carbonyl Carbon Transverse Relaxation Dispersion Measurements and ms-μs Timescale Motion in a Protein Hydrogen Bond Network, J. Biomolecular NMR 29: 187-198 (2004).
J. Patrick Loria, et al., A TROSY CPMG Sequence for Characterizing Chemical Exchange in Large Proteins, J. Biomolecular NMR 15: 151-155 (1999).

(Continued)

*Primary Examiner* — Melissa Koval
*Assistant Examiner* — Rishi Patel
(74) *Attorney, Agent, or Firm* — Eugene F. Derényi; Fogler Rubinoff LLP

(57) ABSTRACT

A slice-selective CPMG pulse sequence with a DANTE-Z selective scheme for measuring spatially-resolved $T_2$ distributions.

3 Claims, 7 Drawing Sheets

(56) References Cited

OTHER PUBLICATIONS

D. Boudot, et al., DANTE-Z. A New Approach for Accurate Frequency Selectivity Using Hard Pulses, J. Magn. Reson. 83(2): 428-439, Jun. 1989.

Christian Roumestand, et al., DANTE-Z, An Alternative to Low-Power Soft Pulses Improvement of the Selection Scheme and Applications to Multidimensional NMR Studies of Proteins, J. Magn. Reson. A 106(2): 168-181, Feb. 1994.

Gareth A. Morris, Ray Freeman, Selective Excitation in Fourier Transform Nuclear Magnetic Resonance, J. Magn. Reson. 29(3): 433-462, Mar. 1978.

R. L. Kleinberg, et al., T1/T2 Ratio and Frequency Dependence of NMR Relaxation in Porous Sedimentary Rocks, J. Colloid. Interface. Sci. 158(1): 195-198, Jun. 1993.

Christian Roumestand, et al., A Practical Approach to the Implementation of Selectivity in Homonuclear Multidimensional NMR with Frequency Selective-Filtering Techniques. Application to the Chemical Structure Elucidation of Complex Oligosaccharides, Magn. Reson. Chem. 37(7): 451-478, Jul. 1999.

Timothy J. Mosher, Michael B. Smith, A DANTE Tagging Sequence for the Evaluation of Translational Sample Motion, Magn. Reson. Med. 15(2): 334-339, Aug. 1990.

Z. H. Cho, et al., FM DANTE Fast Imaging and Variations: Emerging rf-Based Ultrafast Imaging Techniques, Cocepts Magn. Reson. 10(1): 33-54, Dec. 1998.

Christian Roumestand, Daniel Canet, Suppression of Unwanted Sideband Excitations in the DANTE-Z Experiment, J. Magn. Reson. B 106(1): 68-71 (1995).

Katsumi Kose, Visualization of Turbulent Motion using Echo-Planar Imaging with a Spatial Tagging Sequence, J. Magn. Reson. 98: 599-603 (1992).

Klaus Zangger, et al., Pure-Phase Selective Excitation in Fast-Relaxing Systems, J. Magn. Reson. 152(1): 48-56, Sep. 2001.

I. V. Mastikhin, et al., Water Content Profiles with a 1D Centric SPRITE Acquisition, J. Magn. Reson. 156(1): 122-130, May 2002.

M. Halse, et al., Centric Scan SPRITE Magnetic Resonance Imaging: Optimization of SNR, Resolution, and Relaxation Time Mapping, J. Magn. Reson. 169(1): 102-117, Jul. 2004.

M. Mstti Maricq, Application of Average Hamiltonian Theory to the NMR of Solids, Phys. Review B 25(11): 6622-6632, Jun. 1982.

Ad Bax, Correction of Cross-Peak Intensities in 2D Spin-Locked NOE Spectroscopy for Offset and Hartmann-Hahn Effects, J. Magri. Reson 77(1): 134-147, Mar. 1988.

Linqing Li, et al., Spin Echo SPI Methods for Quantitative Analysis of Fluids in Porous Media, J. Magn.Reson. 198(2): 252-260, Jun. 2009.

G. C. Borgia, Uniform-Penalty Inversion of Multiexponential Decay Data, J. Magn. Reson. 132(1): 65-77, May 1998.

A. A. Khrapitchev, et al., Centric-Scan SPRITE Magnetic Resonance Imaging with Prepared Magnetisation, J. Magn. Reson. 181(2): 271-279, Aug. 2006.

\* cited by examiner

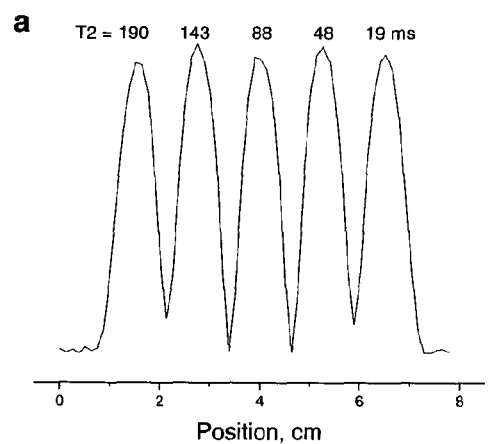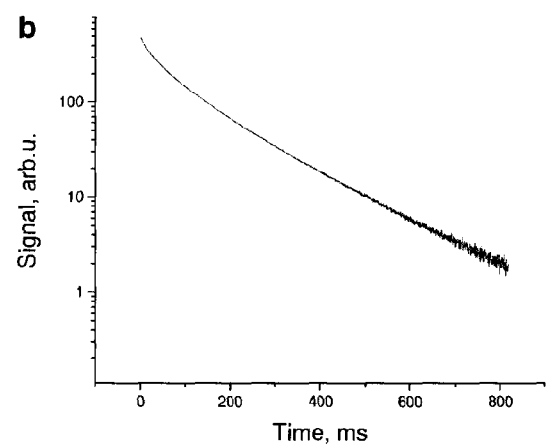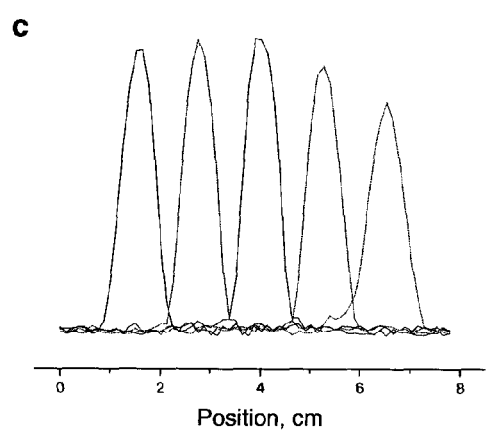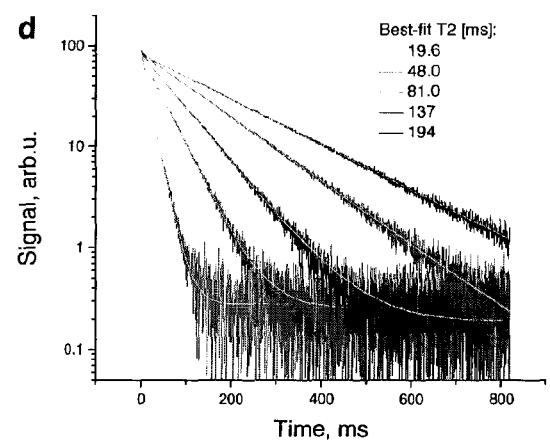
FIGS 4(a) – (d)

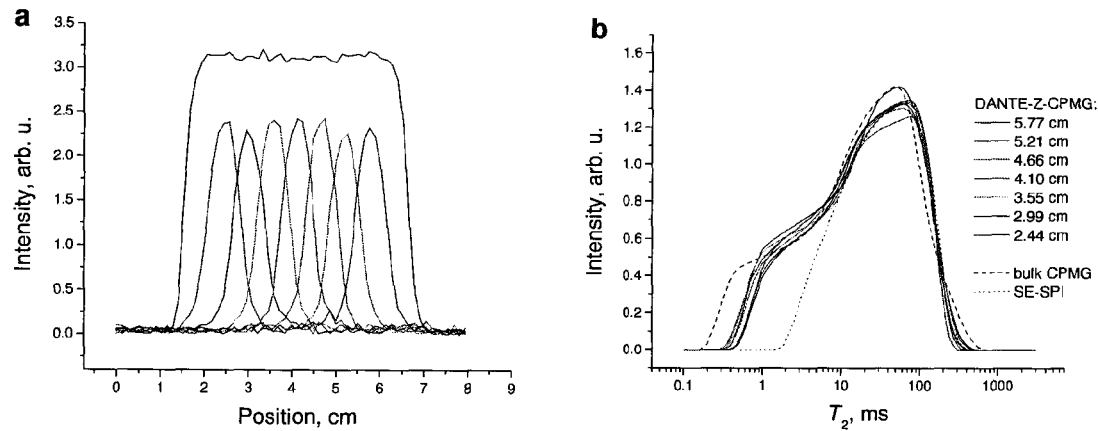
FIGS. 5(a) and (b)
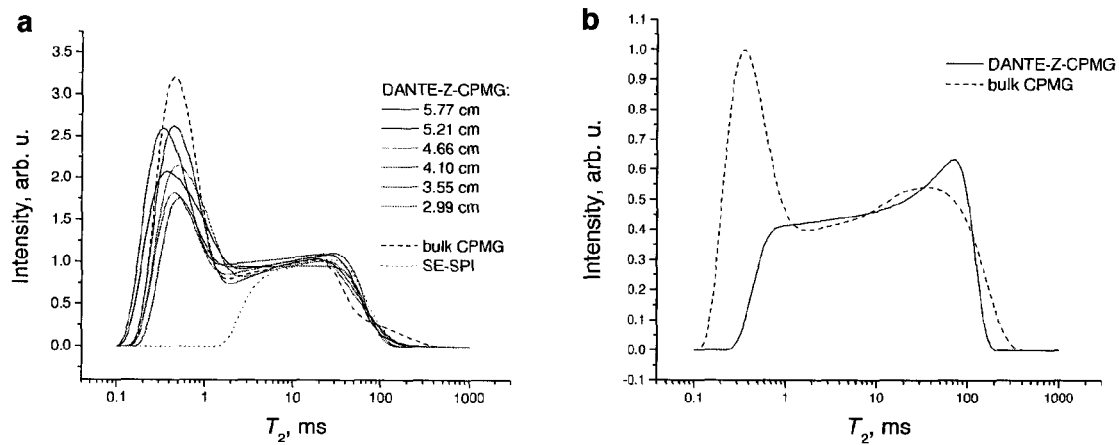
FIGS 6(a) and (b)

US 9,389,193 B1

SPATIALLY RESOLVED MAGNETIC RESONANCE SPIN-SPIN RELAXATION DISTRIBUTION MEASUREMENT METHODS

CROSS-REFERENCE TO RELATED APPLICATIONS

This application claims the benefit of U.S. Provisional Application No. 61/522,978 filed Aug. 12, 2011.

FIELD

The present invention relates to magnetic resonance imaging in general and spatially resolved magnetic resonance spin-spin relaxation distribution measurements in particular.

BACKGROUND

A spatially resolved measurement of $T_2$ relaxation ($T_2$ mapping) is one of the most basic magnetic resonance imaging ("MRI") core analysis measurements employed to determine a wide variety of fluid/matrix properties. MRI employing $T_2$ distribution measurements, including $T_2$ distribution mapping, is an appealing technique for chemical and petroleum engineering, including core analysis, due to its ability to probe the occupancy of pores by water and oil phases [1]. It is suitable, in principle, for studies of a variety of miscible and immiscible processes, including enhanced oil recovery, and for characterizing porous rocks with regard to mass transfer between flowing and stagnant fluids. Recently, it has been recognized to be a promising technique for spatially resolved analysis of the irreducible water saturation of porous rocks [2]. $T_2$ distribution measurements, including $T_2$ distribution mapping, are also widely adopted in clinical applications as well.

It is desirable that a $T_2$ mapping scheme provide as wide an interval of measurable $T_2$ as possible for a comprehensive analysis of relaxation data. Ideally, spatially resolved $T_2$ measurements are expected to give as realistic $T_2$ distributions as regular bulk CPMG measurements. High sensitivity signal-to-noise ratio ("SNR") measurements are also important since low field magnets are traditionally used for core rock analysis.

Two pulse sequences for one-dimensional ("1-D") $T_2$ mapping which employ phase encode magnetic resonance imaging techniques, namely CPMG-prepared SPRITE and spin-echo single-point imaging ("SE-SPI") are described in [3]. The CPMG-prepared SPRITE sequence has no hardware restrictions on the echo timing other than those for a regular CPMG experiment but is relatively slow, as the measurement time is proportional to $T_2$ dimension, and has a worse SNR due to a small radio frequency ("r.f.") pulse flip angle. The spin-echo SPI provides much faster measurements and with good SNR, but has a restriction on the first echo acquisition time. The latter makes it difficult to measure short $T_2$ (<1 ms) characteristic, e.g., for water in clay-containing rocks and cement-based materials.

Prior art MRI based methods are unable to reliably measure short lifetime signal components in a $T_2$ distribution.

SUMMARY OF THE DISCLOSURE

In one implementation, the present disclosure is directed to a method of measuring a signal component in a $T_2$ distribution including using a slice selection method to provide a local $T_2$ measurement through magnetization selected from a specific location through a DANTE-Z method (a known selective excitation method). In a further implementation, the signal component includes more than one signal component and which are short lived signal components.

In another implementation, the present disclosure is directed to a method for generating a magnetic resonance pulse sequence for the investigation of a sample by magnetic resonance, including generating a selective scan; and generating a non-selective scan.

In another implementation, the present disclosure is directed to an MRI based method for measuring spatially-resolved $T_2$ distributions including providing a sample to be imaged; using a slice selection method, providing a local $T_2$ measurement through magnetization selected from a specific location in the sample through a selective excitation method.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 4(a) is a profile (z axis projection) of a stack of five 2 ml cylindrical vials (hereinafter referred to as the "Vials") with $GdCl_3$-doped water, obtained from a regular (prior art) DHK SPRITE measurement;

FIG. 4(b) is a bulk CPMG decay from the Vials of FIG. 4(a), a superposition of five components with $T_2$=190, 143, 88, 48 and 19 ms;

FIG. 4(c) are individual profiles the Vials of FIG. 4(a), selected by DANTE-Z SPRITE according to an embodiment of the invention;

FIG. 4(d) show $T_2$ decays from selected areas obtained with a DANTE-Z-CPMG method according to an embodiment of the invention and their best-fit single-exponential models;

FIG. 5(a) is a profile of Berea sandstone saturated with water obtained by DHK SPRITE and slices by DANTE-Z-SPRITE according to an embodiment of the invention, selected for $T_2$ measurements;

FIG. 5(b) show $T_2$ distributions obtained with a DANTE-Z-CPMG method according to an embodiment of the invention at positions shown in FIG. 5(a), compared to bulk CPMG distribution (dashed line) and that from the central pixel's decay in SE-SPI experiment (dotted line);

FIG. 6(a) show $T_2$ distributions obtained with a DANTE-Z-CPMG method according to an embodiment of the invention at the indicated positions along 5-cm sample of water-saturated sandstone #15, compared to bulk CPMG distribution (dashed line) and that from the central pixel's decay in SE-SPI experiment (dotted line);

FIG. 6(b) show a comparison of $T_2$ distributions by a DANTE-Z-CPMG method according to an embodiment of the invention, and bulk CPMG in water-saturated Wallace sandstone shows a worse performance of DANTE-Z-CPMG than in the case of sandstone #15.

DETAILED DESCRIPTION

Certain embodiments of the invention include a slice-selective CPMG pulse sequence with a DANTE-Z selective scheme for measuring spatially-resolved $T_2$ distributions. This is also referred to by the inventors as DANTE-Z-CPMG.

Certain embodiments of the invention include a method of measuring spatially-resolved $T_2$ which is based on a slice selective CPMG sequence. Only $T_2$ at a particular spatial position is measured at a time. There are a number of applications where only monitoring of $T_2$ at particular locations is required. For example, if a sample has well-defined large-scale heterogeneities, only $T_2$ relaxation someplace in those heterogeneous regions may be of interest. Another case is when one monitors $T_2$ change during a long repetitive experiment (e.g., a core flood experiment) and, to avoid processing a large amount of data, analyzes $T_2$ relaxation only from few chosen locations.

The DANTE-Z [4; 5] method is based on a selective inverting a DANTE sequence [6], a series of short pulses which act as an effective 180° pulse upon a band of resonance frequencies. Since the magnetization selected by this pulse train lies along z axis, it is affected only by $T_1$ relaxation while waiting for eddy currents to settle after a slice gradient, which is advantageous for short $T_2$ samples with $T_1>T_2$ (the latter inequality is typical for water in rocks [7]). For the same reason, it does not introduce any phase problems when combined with another pulse sequence, which may take place for the selective excitation with a global flip angle of 90° when two transverse components of magnetization are created. Besides, it is easy to program and can be implemented on "routine spectrometers, without the need for sophisticated hardware"[8].

Certain embodiments of the invention include supplementing the slice-selective CPMG $T_2$ mapping method with an MRI sequence employing the DANTE-Z selective excitation scheme, in order to visualize the slice of interest. In certain embodiments, a one-time running of such an MRI sequence prior to the slice-selective CPMG helps one to adjust the width and the location of the slice.

The DANTE-Z Selective Excitation Scheme

Figure 1:
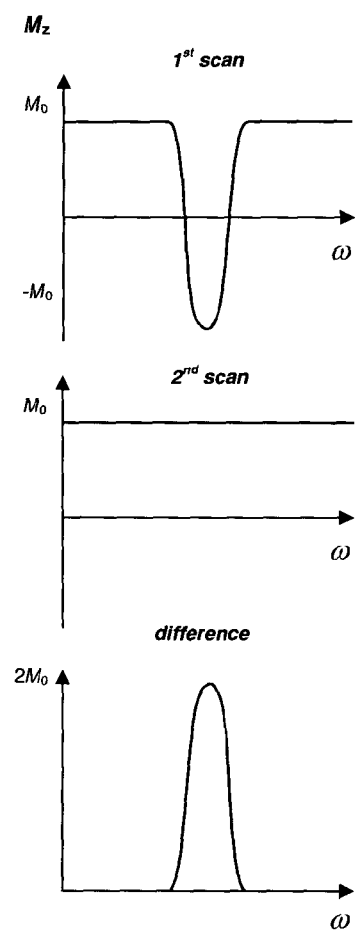
FIG. 1 is an illustration of the prior art DANTE-Z acquisition scheme.

The DANTE-Z scheme consists of two successive scans: during the first scan, the magnetization is inverted from z to −z within a selected band of resonance frequencies, and during the second scan, it is all maintained along z. Subtracting the signals coming from those scans leaves only selected frequency components in the resulting signal, no matter what happens to the magnetization outside the frequency band after applying DANTE-Z (see FIG. 1). The pulse sequence realizing this scheme is known in the art from the article [10] and can be written as:

$$[\theta-\theta_{\pm x}-\tau]_n-\alpha_x-Acq_\pm \quad (1)$$

where $2n\theta=180°$ and a denotes a pulse that brings the z magnetization to the transverse plane for acquisition or precession purposes. The sequence (1) differs from a basic DANTE pulse train in that the second θ-pulse has been found to cancel all negative sidebands at $(2k+1)/2\tau$ Hz, so that the first (positive) sideband appears only at $1/\tau$ Hz from the central frequency. This diminishes the problem of multiple selective excitation.

Figure 2:
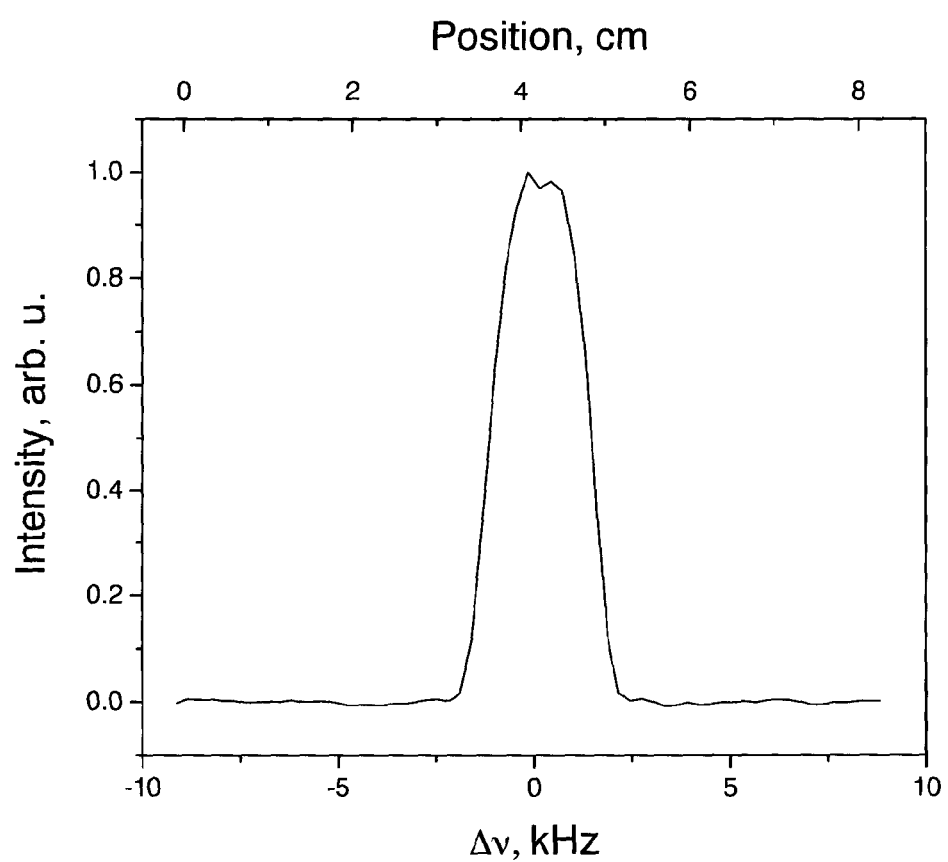
FIG. 2 is a selectivity profile of the prior art DANTE-Z sequence (1) with n=40, τ=40 μs and a sinc-modulated θ pulses. The profile is a central slice from a rectangular object (a vial of doped water), acquired in a DANTE-Z-SPRITE experiment (see below) with a slice gradient strength of 0.5 G/cm.

DANTE-Z has been shown to yield a good selectivity profile with reduced side lobes as compared to a conventional DANTE sequence with a 90° flip angle [10]. In order to remove the side lobes completely and to improve the profile toward a quasi-rectangular shape, the amplitude of θ pulses is modulated by a sinc function [9; 11]. The resulting profile is shown in FIG. 2. The sequence (1) differs from in that the second θ pulse is applied immediately after the first one. The pairwise application of θ pulses cancels all negative sidebands at $(2k+1)/2\tau$ Hz, which appear in the basic DANTE-Z sequence [4], so that the first (positive) sideband appears only at $1/\tau$ Hz from the central frequency [10]. This helps one to avoid more effectively a multiple selective excitation (see below).

$T_2$ Mapping Sequences

Figure 3A:
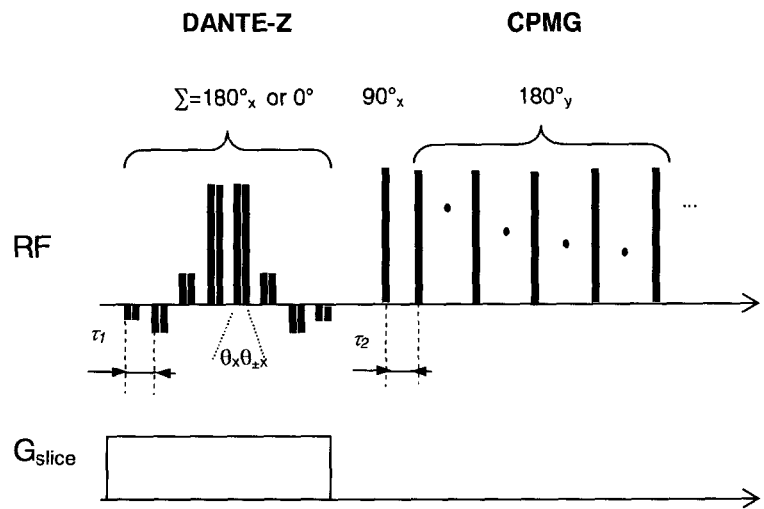
FIG. 3(a) is a DANTE-Z-CPMG pulse sequence according to an embodiment of the invention.
Figure 3B:
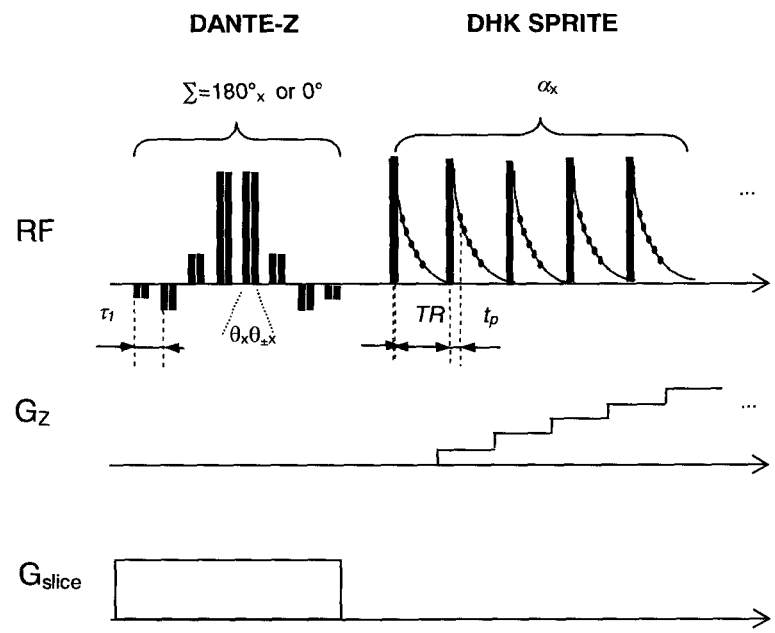
FIG. 3(b) is a DANTE-Z-SPRITE pulse sequence according to an embodiment of the invention. During the first scan, θ pulses in all pairs in DANTE-Z have the same phase providing the total flip angle of 180° for selected frequencies. During the second scan, the θ pulses in the pairs are anti-phase with the total flip angle of zero; the rest of the pulse sequence parameters staying unchanged. The acquired signal is a difference between the two scans.

FIG. 3 (a) shows a DANTE-Z-CPMG sequence according to an embodiment of the invention. The sequence comprises a combination of DANTE-Z given by sequence (1) with a regular CPMG pulse train. Here and in all following sequences, DANTE-Z with n=40 and τ=40 μs is used, and the CPMG 180° pulse period is 0.4 ms. There is a delay for eddy currents between the switching off of the slice gradient and applying the CPMG train, which is 300 μs for a the gradient coil used. Including this delay, the total duration of the DANTE-Z slice selection block approaches 2 ms. The slice thickness is varied by the gradient strength, while the position of the slice is controlled by the carrier frequency of the 0 pulses.

The same DANTE-Z block is used in an auxiliary MRI sequence, which is intended for visualization and adjustment of the slice of interest. In one embodiment of the invention, SPRITE, a purely phase encoding MRI technique, namely its double half k-space (DHK) variant [12], is chosen for this purpose The intrinsic idea of DANTE-Z, to subtract the signals acquired with the alternate storage of the magnetization along ±z axis, well suits SPRITE, where the subtraction is needed when one wants to remove the steady-state component of the SPRITE signal and thereby to make the image intensity be proportional to a prepared magnetization [13]. Thus, no modification is required of the acquisition scheme of SPRITE with prepared magnetization [3; 13]. A diagram of a DANTE-Z/DHK SPRITE sequence according to an embodiment of the present invention is shown in FIG. 3 (b). To improve SNR, four FID points are acquired after every a pulse, following by the chirp-z transform of the acquired k-space data for the image reconstruction [14].

Test Measurements

Sequences according to the invention were tested on a set of five 2 ml cylindrical vials of water doped with $GdCl_3$, stacked together in a raw of 6 cm long. $T_2$ of water in the vials varied as 19, 48, 88, 143 and 190 ms. The profile of such a composite sample is shown in FIG. 4(a), as obtained with a regular (non-selective) DHK SPRITE, and FIG. 4(b) shows bulk CPMG measurements on this sample.

Applying the slice gradient of 0.78 G/cm and changing the carrier frequency of 0 pulses from −10 to 10 kHz with respect to the central frequency, individual vials could be selected with good accuracy (FIG. 4(c)). The DANTE-Z-CPMG measurements undertaken at those individual vials' positions give one-exponential decays with $T_2$ that agree very well with the reference values (FIG. 4(d)). The back extrapolated amplitudes of the decays are all about one-fifth of that of the bulk (non-selective) CPMG decay. These data demonstrate the accuracy of the technique at measuring $T_2$ as well as its ability to preserve the quantitative information about the spin density at chosen positions. Note that no sideband appears even if the slice is moved close the edges of the 8-cm field of view.

The next experiment was carried out on three sandstone samples—Berea, sandstone #15 and Wallace, all saturated with water, to test the goodness of the DANTE-Z-CPMG sequence at measuring $T_2$ distributions. FIG. 5(a) shows the whole profile of the Berea sample and the slices chosen for measuring $T_2$ distributions, and the distributions are shown in FIG. 5(b), in the respective colors. The distributions by DANTE-Z-CPMG virtually coincide with the bulk $T_2$ measurements obtained in a regular CPMG experiment (FIG. 5(b), dash line). This is a noticeable improvement compared to SE-SPI $T_2$ mapping technique presented earlier [3] (FIG. 5(b), dot line). The next sample, water-saturated sandstone #15, is more challenging than Berea for its two-humped $T_2$ distribution with a pronounced peak at $T_2$ 0.5 ms (FIG. 6(a), dash line). Nevertheless, the peak is well reproducible in DANTE-Z-CPMG measurements (FIG. 6(a)). Again, this considerably exceeds the limit of SE-SPI for short $T_2$ (FIG. 6(a), dot line). The bulk $T_2$ distribution in the third sample, Wallace sandstone, exhibits a very similar to sandstone #15 peak at $T_2$ 0.4 ms (FIG. 6(b), dash line). However, this peak is now irreproducible in DANTE-Z-CPMG measurements (FIG. 6(b), line 2). Such different performance of DANTE-Z-CPMG for sandstone #15 and Wallace can be explained by the difference in their $T_1$ distributions. In Wallace, the latter stretches a wide interval of 1 ms to 2 s, while in sandstone #15 it is considerably narrower, ranging only from 0.5 ms to 0.4 s. A narrow $T_1$ distribution means that components with different relaxivity are attenuated more similarly during the selective pulses and following storage period, thus better preserving the relative intensities in the CPMG signal.

Figures 7A, 7B, 7C, 7D:
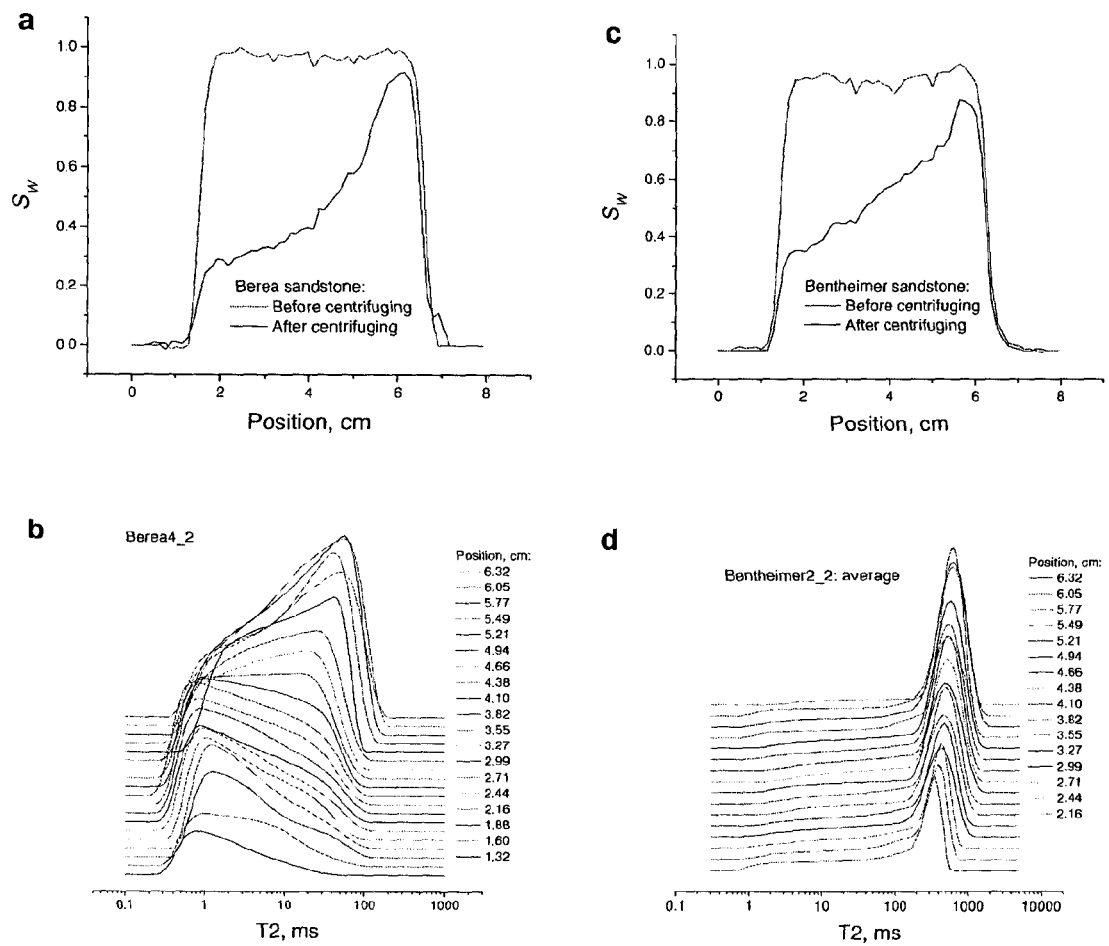
FIG. 7(a) show SPRITE profiles of a 5-cm cylindrical core of Berea sandstone saturated with water, recorded before and after 3.5 hrs centrifuging at 2000 r.p.m.
FIG. 7(b) show $T_2$ distributions measured with a DANTE-Z-CPMG method according to an embodiment of the invention at different positions along the partly de-saturated Berea sample.
FIGS. 7(c) and 7(d) show the same sort of data as in FIGS. 7(a) and 7(b) but for Bentheimer sandstone; and, FIG. 8 schematically shows an MRI measuring system which is suited for carrying out methods according to embodiments of the present invention.

For the last test, DANTE-Z-CPMG was applied to water-filled Berea and Bentheimer sandstone core samples that had been partly de-saturated by 3.5-hrs centrifuging at 2000 r.p.m. Profiles of the samples in their initial and de-saturated states are shown in FIGS. 7(a, c). The goal of these experiments was to generate within a porous rock sample a variable water saturation and to measure associated variable $T_2$ distributions. This type of measurements have been conducted with the SE-SPI technique [2]. The previous tests show, however, that using DANTE-Z-CPMG instead of SE-SPI permits a more accurate evaluation of the $T_2$ distribution, particularly for the short $T_2$ components. FIGS. 7(b and d) show $T_2$ distributions measured by DANTE-Z-CPMG at different positions along partly de-saturated Berea and Bentheimer core samples, respectively. The obtained distributions can be further analyzed in the terms of average $T_2$ values, which have been found to correlate with $S_W$ [2], to estimate the irreducible water saturation.

The tests above show that DANTE-Z-CPMG can probe $T_2$ components down to 0.2 ms. This presents a noticeable advantage over SE-SPI, the previous $T_2$ mapping technique we introduced for porous solids (see FIGS. 5(b) and 6(a)).

The ability of DANTE-Z-CPMG to measure that short $T_2$ is, however, not general but depends on $T_1$ relaxation of the sample. Thus, the comparison of sandstone #15 and Wallace, having similar peaks at $T_2$~0.4-0.5 ms, demonstrates a worse performance of DANTE-Z-CPMG in the latter case. This can be explained by different $T_1$ distributions in those samples (see above). The spread of $T_1$'s may manifest itself during both the lengthy selective inversion and the following storage period, when the different $T_1$ components experience different attenuation. In this case, a narrow $T_1$ distribution is favorable for the DANTE-Z-CPMG performance. The storage period is necessary for eddy currents to settle down after the slice gradient and amounts for the hardware used in the experiments to 0.3 ms. The same delay is applied in SE-SPI after the encoding gradient inserted between 90° and first 180° pulses [3]. Together with the encoding period, it shifts the first echo acquisition time in SE-SPI to 1.2-1.6 ms after excitation, causing an irrevocable loss of $T_2$ components shorter than 1-2 ms (see FIG. 6(a)). In DANTE-Z-CPMG, the acquisition delay is considerably shorter and it affects $T_2$ distribution only via $T_1$ mechanism of relaxation, as mentioned above, thus providing better-fitting $T_2$ distributions than in SE-SPI for short $T_2$ components.

EXPERIMENTAL

NMR measurements were carried out on an Oxford Instruments Maran DRX spectrometer equipped with a 0.35 T horizontal bore magnet (v=15 MHz), at room temperature. The r.f. probe used was a home-made 54-mm wide birdcage probe with a 90°-pulse duration of 19 μs. The acquisition parameters can be found in the text and figures captions. $T_2$ distributions were measured by using a Laplace inverse transform algorithm UPEN [15].

The natural sandstone samples used in the tests have the following characteristics. Berea: porosity ϕ=22%, permeability κ=100-200 mD; sandstone #15: ϕ=16%, κ=7 mD; Wallace: porosity ϕ=14%, κ=0.1 mD; Bentheimer: porosity ϕ=24%, κ~1 D.

Figure 8:
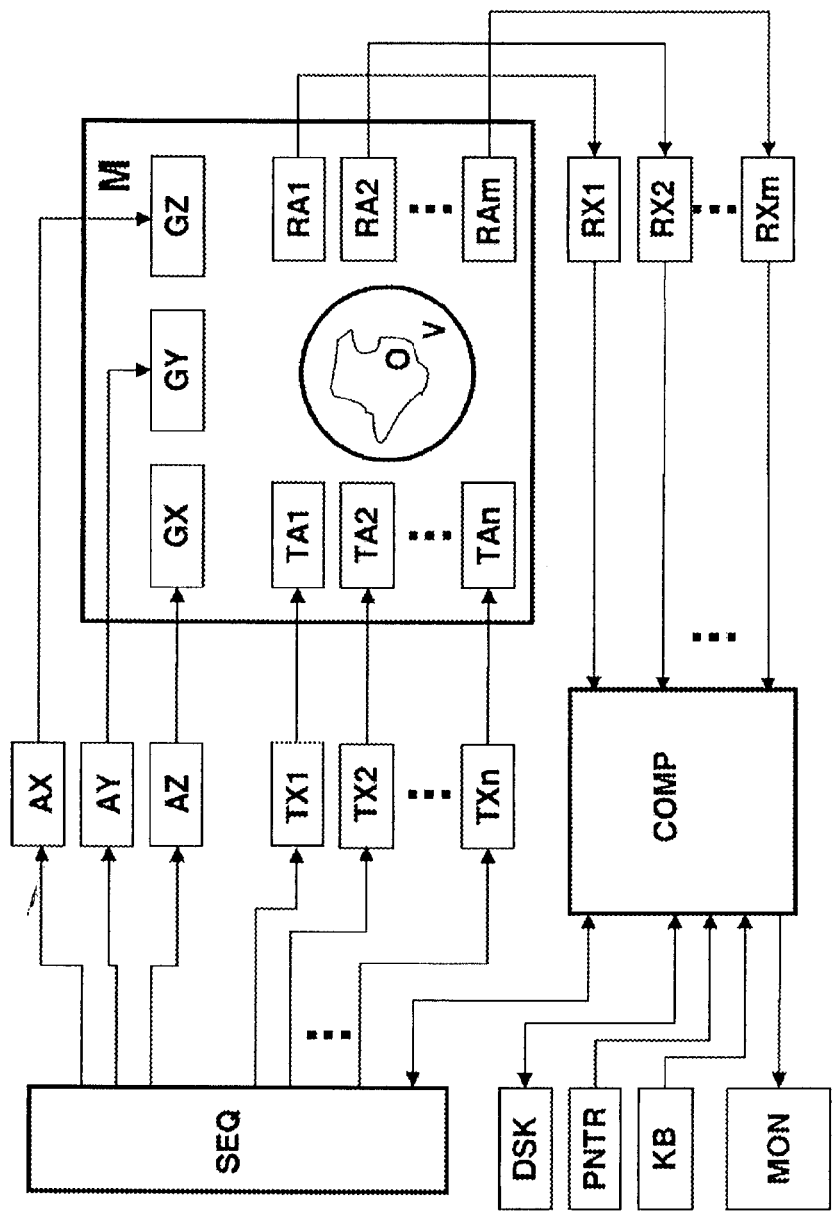

The invention can be implemented in a conventional MRI instrument apparatus as a programmed pulse sequence. For example, FIG. 8 schematically shows an MRI measuring system which is suited for performing the inventive method. The system contains a main magnet M for generating the basic magnetic field which is substantially homogeneous and static in a volume under investigation V. Three sets of gradient coils GX, GY, and GZ are introduced into the bore of the main magnet M, which surround the volume under investigation V, and can superpose additional magnetic fields of controllable duration and strength with constant gradients on the basic field. Gradient amplifiers AX, AY, and AZ, which are driven by a sequence control unit SEQ for timely generation of gradient pulses, provide the gradient coils GX, GY, GZ with electric current for generating substantially linear gradient fields.

Several transmitting elements TA1 to TAn are located in the gradient field system, the entirety of which is also called transmitting antenna means. They surround an object under investigation O and are fed by several independent RF power transmitters TX1 . . . TXn. The RF pulses generated by these RF power transmitters TX1 . . . TXn are determined by the sequence control unit SEQ and triggered at the correct time. The transmitting elements TA1 to TAn irradiate RF pulses onto the object under investigation O located in the volume under investigation V (as described in more detail in FIG. 8), thereby exciting the nuclear spins. The resulting magnetic resonance signals are converted into electric voltage signals using one or more RF receiver elements RA1, ..., RAm, which are then supplied to a corresponding number of receiver units RX1, ..., RXm. The overall receiver elements RA1, ..., RAm are also called receiver antenna means that consists of m receiver elements RA1, ..., RAm. These are also located within the gradient coils GX, GY, GZ and surround the object under investigation O. In order to reduce the expense for equipment, the transmitting and receiver antenna means may also be designed and connected in such a fashion that one or more of the transmitting elements TA1 to TAn are also used for receiving the magnetic resonance signals. In this case, which is not considered in FIG. 8, switching over between transmitting and receiving operation is effected by one or more electronic transmitting-receiver switch points that are controlled by the sequence control unit SEQ. This means that during the RF transmitting phases of the executed RF pulse sequence, this antenna(s) is/are connected to the corresponding RF power transmitter(s) and is/are separated from the allocated receiver channels, while for the receiver phases, the transmitters are separated and the receiver channel is connected. The received signals are amplified by the receiving units RX1 to RXm shown in FIG. 1, and are converted into digital signals using conventional signal processing methods, and passed on to an electronic computer system COMP. In addition to the reconstruction of images and spectra and values derived from the received measured data, the controlling computer system COMP serves to operate the entire MRI measuring system and initiates performance of the pulse sequences through corresponding communication with the sequence control unit SEQ. The user-controlled or automatic execution of programs for adjusting the measuring system properties and/or for generating magnetic resonance images is also provided on this control computer system COMP, as well as the display of the reconstructed images, storage and management of measurement and image data and control programs. In order to perform these tasks, this computer system has at least one processor, one working memory, one computer keyboard KB, one display instrument PNTR, e.g. a computer mouse, one screen MON and one external digital storage unit DSK.

REFERENCES

[1] G. R. Coates, L. Xiao, and M. G. Prammer, NMR logging: principles and applications Halliburton Energy Services, Houston, 1999.
[2] L. Li, H. Han, and B. J. Balcom, Spin echo SPI methods for quantitative analysis of fluids in porous media. Journal of Magnetic Resonance 198 (2009) 252-260.
[3] O. V. Petrov, G. Ersland, and B. J. Balcom, $T_2$ distribution mapping profiles with phase encode MRI. Journal of Magnetic Resonance in print (2011).
[4] D. Boudot, D. Canet, J. Brondeau, and J. C. Boubel, DANTE-Z—A new approach for accurate frequency-selectivity using hard pulses. Journal Of Magnetic Resonance 83 (1989) 428-439.
[5] C. Roumestand, D. Canet, N. Mahieu, and F. Toma, DANTE-Z, an alternative to low-power soft pulses—improvement of the selection scheme and applications to multidimensional NMR-studies of proteins. Journal of Magnetic Resonance Series A 106 (1994) 168-181.
[6] G. A. Morris, and R. Freeman, Selective excitation in fourier-transform nuclear magnetic-resonance. Journal of Magnetic Resonance 29 (1978) 433-462.
[7] R. L. Kleinberg, S. A. Farooqui, and M. A. Horsfield, $T_1/T_2$ ratio and frequency-dependence of nmr relaxation in porous sedimentary-rocks. Journal of Colloid and Interface Science 158 (1993) 195-198.
[8] C. Roumestand, C. Delay, J. A. Gavin, and D. Canet, A practical approach to the implementation of selectivity in homonuclear multidimensional NMR with frequency selective-filtering techniques. Application to the chemical structure elucidation of complex oligosaccharides. Magnetic Resonance in Chemistry 37 (1999) 451-478.
[9] Z. H. Cho, Y. M. Ro, and I. K. Hong, FM DANTE fast imaging and variations: Emerging rf-based ultrafast imaging techniques. Concepts in Magnetic Resonance 10 (1998) 33-54.
[10] C. Roumestand, and D. Canet, Suppression of unwanted sideband excitations in the DANTE-Z experiment. Journal of Magnetic Resonance B106 (1995) 68-71.
[11] K. Kose, Visualization of turbulent motion using echo-planar imaging with a spatial tagging sequence. Journal of Magnetic Resonance 98 (1992) 599-603.
[12] I. V. Mastikhin, H. Mullally, B. MacMillan, and B. J. Balcom, Water content profiles with a 1D centric SPRITE acquisition. Journal of Magnetic Resonance 156 (2002) 122-130.
[13] A. A. Khrapitchev, B. Newling, and B. J. Balcom, Centric-scan SPRITE magnetic resonance imaging with prepared magnetisation. Journal of Magnetic Resonance 181 (2006) 271-279.
[14] M. Halse, J. Rioux, S. Romanzetti, J. Kaffanke, B. MacMillan, I. Mastikhin, N. J. Shah, E. Aubanel, and B. J. Balcom, Centric scan SPRITE magnetic resonance imaging: optimization of SNR, resolution, and relaxation time mapping. Journal of Magnetic Resonance 169 (2004) 102-117.
[15] G. C. Borgia, R. J. S. Brown, and P. Fantazzini, Uniform-penalty inversion of multiexponential decay data. Journal of Magnetic Resonance 132 (1998) 65-77.

We claim:

1. A method for generating a magnetic resonance pulse sequence for the investigation of a sample by magnetic resonance, comprising:
    generating a selective scan;
    wherein, the selective scan comprises a first magnetic resonance pulse sequence wherein the magnetization is inverted from z to −z inside a frequency band, and the Pulse sequence is represented by $[\theta_x - \theta_{\pm x} - \tau]_n$, where $2n\theta = 180°$, with successive RF pulses of rotation angle $\theta$, having identical phases, with delay times $\tau$, repeated n times;
    following the selective scan with a CPMG pulse sequence;
    generating a non-selective scan;
    wherein the non-selective scan comprises generating a second magnetic resonance pulse sequence wherein the magnetization is maintained along z;
    applying a magnetic field gradient during the first magnetic pulse sequence, such that a range of frequencies are created in the sample in the direction of the magnetic field gradient;
    obtaining a first signal from the selective scan;
    obtaining a second signal from the non-selective scan; and,
    subtracting the first and second signals to obtain a resulting signal with only selected frequency components for slice selective investigation of the sample.

2. The method of claim 1, wherein the non-selective scan further comprises modulating a pulse sequence which produces a zero net rotation of the magnetization of the sample according to $[\theta_x - \theta_{\pm x} - \tau]_n$, where $2n\theta = 0°$, with successive RF pulses of rotation angle $\theta$, having opposed phases, with delay times $\tau$, repeated n times:

following the non-selective scan with a CPMG pulse sequence.

3. The method of claim 1, further comprising obtaining a spatially-resolved $T_2$ distribution from the resulting signal decay in the selected slice.

\* \* \* \* \*